US011651855B2

(12) United States Patent
Sadhvani et al.

(10) Patent No.: US 11,651,855 B2
(45) Date of Patent: May 16, 2023

(54) SYSTEMS AND METHODS FOR MANAGING AND UPDATING CONTEXTUAL INTELLIGENT PROCESSES USING ARTIFICIAL INTELLIGENCE ALGORITHMS

(71) Applicant: Aetna Inc., Hartford, CT (US)

(72) Inventors: Dinesh Sadhvani, Hartford, CT (US); Robert W. Goldman, Hartford, CT (US)

(73) Assignee: Aetna Inc., Hartford, CT (US)

(*) Notice: Subject to any disclaimer, the term of this patent is extended or adjusted under 35 U.S.C. 154(b) by 267 days.

(21) Appl. No.: 16/850,820

(22) Filed: Apr. 16, 2020

(65) Prior Publication Data

US 2021/0327572 A1 Oct. 21, 2021

(51) Int. Cl.
*G16H 40/67* (2018.01)
*G16H 20/00* (2018.01)
*G06N 5/02* (2023.01)

(52) U.S. Cl.
CPC .......... *G16H 40/67* (2018.01); *G16H 20/00* (2018.01); *G06N 5/02* (2013.01)

(58) Field of Classification Search
CPC ......... G16H 10/00–80/00; G06N 3/00–99/007
See application file for complete search history.

(56) References Cited

U.S. PATENT DOCUMENTS

| 7,983,934 | B1 * | 7/2011 | Sholtis | G16H 20/10 |
| | | | | 705/2 |
| 10,043,591 | B1 * | 8/2018 | LaBorde | G06N 3/08 |
| 10,248,653 | B2 * | 4/2019 | Blassin | G06N 20/00 |
| 10,805,462 | B1 * | 10/2020 | Ginter | H04L 67/563 |
| 11,152,107 | B2 * | 10/2021 | Cardonha | G16H 40/20 |
| 11,551,817 | B2 * | 1/2023 | Myers | G16H 50/20 |

(Continued)

FOREIGN PATENT DOCUMENTS

WO WO-2014096118 A2 * 6/2014 ............ G06F 16/22

OTHER PUBLICATIONS

Gil et al., "Internet of Things: A Review of Surveys Based on Context Aware Intelligent Services," Sensors 2016, 16, 1069; (Year: 2016).*

(Continued)

*Primary Examiner* — Jonathon A. Szumny
(74) *Attorney, Agent, or Firm* — Leydig, Voit & Mayer, Ltd.

(57) ABSTRACT

In some instances, the disclosure provides a method for managing and updating contextual intelligent processes using artificial intelligence algorithms. The method comprises obtaining, from a user device, health information indicating a health triggering event associated with a user, obtaining event information associated with the user, determining, based on the health triggering event, one or more contextual intelligent processes for the health triggering event, retrieving one or more contextual artificial intelligence datasets, updating the one or more contextual intelligent processes with at least one new service based on inputting the health triggering event, the event information, and the one or more contextual intelligent processes into the one or more contextual artificial intelligence datasets, and performing the one or more updated contextual intelligent processes.

19 Claims, 8 Drawing Sheets

(56) References Cited

U.S. PATENT DOCUMENTS

| | | | | |
|---|---|---|---|---|
| 2004/0034288 A1* | 2/2004 | Hennessy | ............... | G16H 20/10 600/300 |
| 2005/0075542 A1* | 4/2005 | Goldreich | .............. | G16H 40/67 600/300 |
| 2008/0061961 A1* | 3/2008 | John | .................. | A61N 1/37258 600/300 |
| 2012/0035957 A1* | 2/2012 | Hanz | ...................... | G16H 20/10 705/3 |
| 2012/0290311 A1* | 11/2012 | Tara | ....................... | G16H 40/20 705/2 |
| 2012/0303387 A1* | 11/2012 | Walton, III | ............ | G16H 10/65 705/3 |
| 2014/0269509 A1* | 9/2014 | Ramachandran | ....... | H04L 67/24 370/328 |
| 2015/0046388 A1* | 2/2015 | Sheth | ..................... | G06N 5/022 706/55 |
| 2015/0142871 A1* | 5/2015 | Tofighbakhsh | ......... | H04W 4/60 709/203 |
| 2015/0161351 A1* | 6/2015 | Scalpati | ................. | G16H 10/60 705/2 |
| 2016/0085927 A1* | 3/2016 | Dettinger | ............... | G06Q 10/00 705/2 |
| 2016/0248698 A1* | 8/2016 | Sahu | ................... | H04L 67/1001 |
| 2016/0335410 A1* | 11/2016 | Swank | .................. | H04W 8/183 |
| 2017/0109479 A1* | 4/2017 | Vemireddy | ............ | G06Q 50/22 |
| 2017/0323485 A1* | 11/2017 | Samec | .................... | G06F 3/013 |
| 2018/0000346 A1* | 1/2018 | Cronin | ..................... | A61B 5/00 |
| 2018/0036591 A1* | 2/2018 | King | ..................... | A63B 24/0075 |
| 2018/0054710 A1* | 2/2018 | Gum | ...................... | G16H 50/30 |
| 2018/0101657 A1* | 4/2018 | Kochura | ................ | G16H 50/30 |
| 2020/0098464 A1* | 3/2020 | Velado | ................. | A61B 5/4839 |
| 2020/0334871 A1* | 10/2020 | Su | ........................ | A61B 8/5269 |
| 2020/0357384 A1* | 11/2020 | Kim | ...................... | G06N 3/0445 |
| 2020/0401465 A1* | 12/2020 | Douglas | ................ | G16H 40/00 |
| 2021/0319866 A1* | 10/2021 | Ahmed | .................. | G16H 40/67 |
| 2021/0350889 A1* | 11/2021 | Kantor | ................... | G16H 20/10 |

OTHER PUBLICATIONS

Bottazzi et al., "Context-Aware Middleware Solutions for Anytime and Anywhere Emergency Assistance to Elderly People," IEEE Communications Magazine • Apr. 2006 pp. 86-90 (Year: 2006).*

* cited by examiner

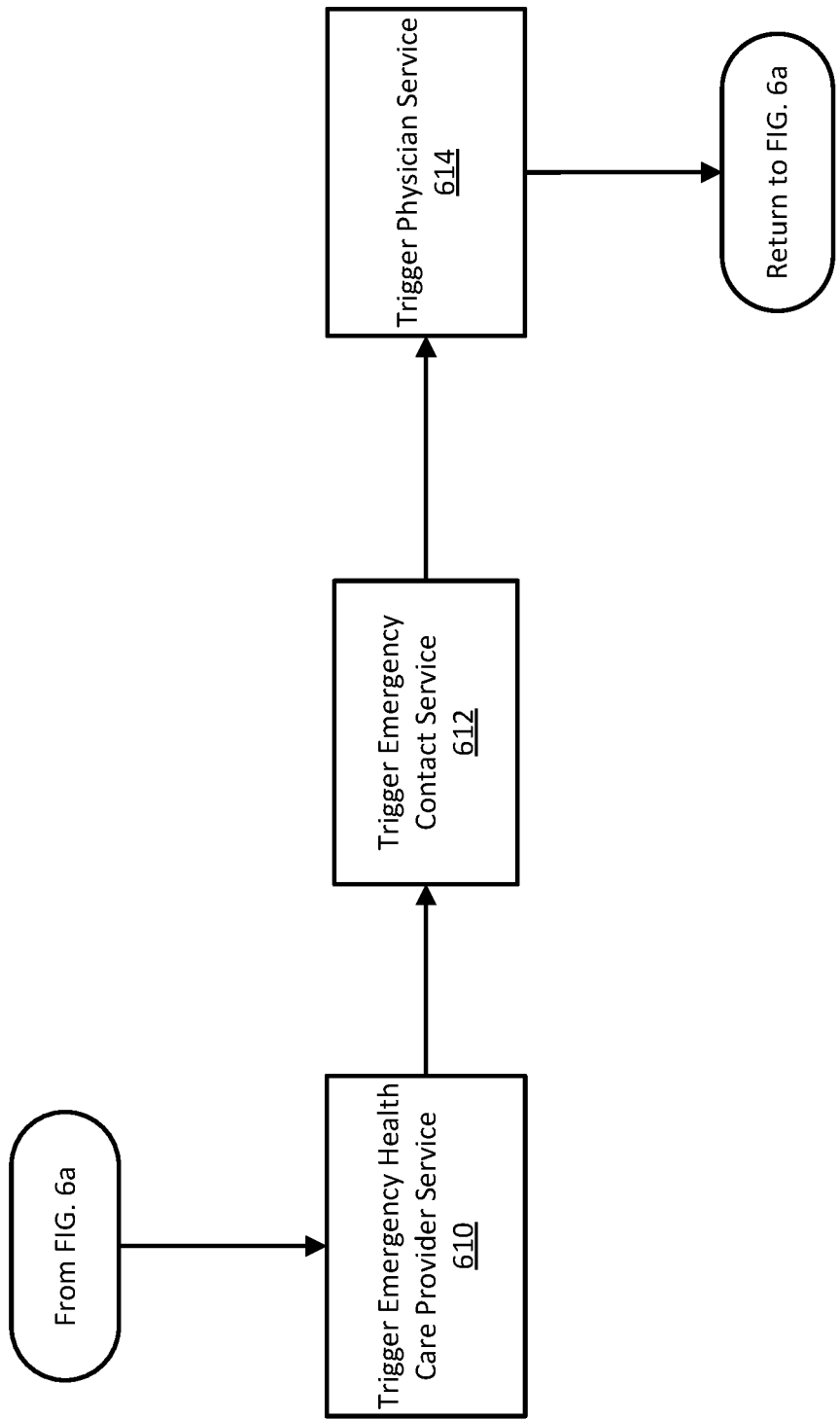

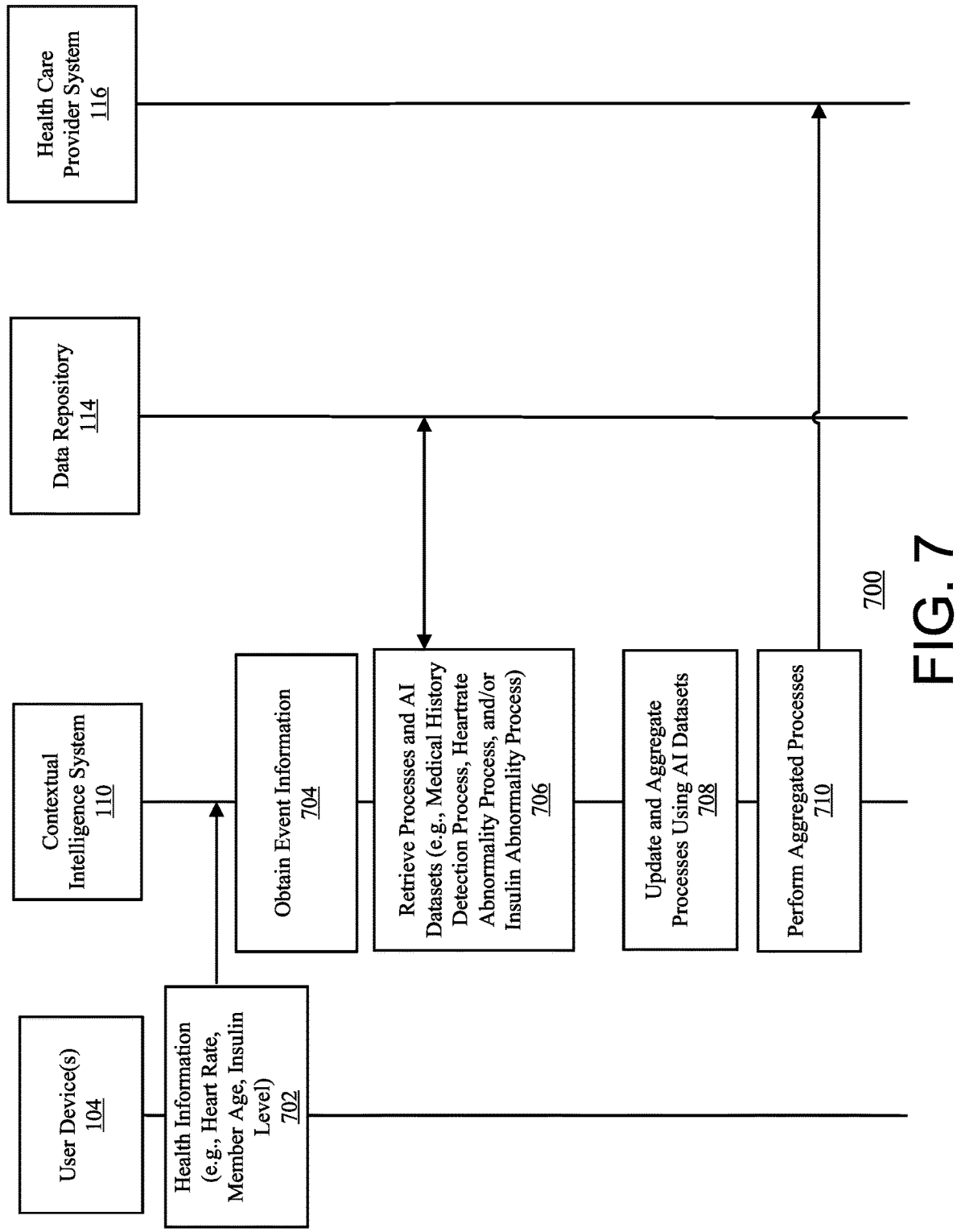

SYSTEMS AND METHODS FOR MANAGING AND UPDATING CONTEXTUAL INTELLIGENT PROCESSES USING ARTIFICIAL INTELLIGENCE ALGORITHMS

BACKGROUND

Enterprise organizations may develop software applications to alert users of medically relevant information pertaining to them or their families. For instance, enterprise organizations may receive user information from the user's mobile device and then identify and alert the user of a medically pertinent condition or event. However, to remain competitive and provide better service for their users, the enterprise organization may seek to perform further steps such as developing processes or workflows directed at the specific medically pertinent condition or event. For example, if the user has diabetes and the enterprise organization receives information indicating an insulin level that is outside of a normal range, the enterprise organization may provide a certain process to assist the user at that time.

Typically, each of these processes or workflows includes a series of actions, steps, decisions, or rules that invoke one or more services hosted by different computing platforms or data centers. For example, the insulin process or workflow may invoke services hosted by different computing platforms including health provider computing platforms and/or even emergency service computing platforms. Generally, each of these actions, steps, decisions, and/or rules include code that is fairly static (i.e., code that is unable to be changed once implemented). However, the needs of users or other extraneous factors (e.g., weather and so on) may impact the processes and workflows in real-time. For example, due to severe weather, the user might not be able to pick up their medical prescription and instead may require emergency service. Accordingly, there remains a technical need to update these processes in real-time so that users may receive the most optimal treatment at all times.

SUMMARY

In some instances, the disclosure provides a method for managing and updating contextual intelligent processes using artificial intelligence algorithms. The method comprises obtaining, from a user device and by a contextual intelligence system, health information indicating a health triggering event associated with a user. The method further comprises obtaining, by the contextual intelligence system, event information associated with the user. The method further comprises determining, by the contextual intelligence system and based on the health triggering event, one or more contextual intelligent processes for the health triggering event, wherein each of the one or more contextual intelligent processes comprises a sequence of actions, and wherein the sequence of actions comprises invoking a first service hosted on a first computing platform. The method further comprises retrieving, by the contextual intelligence system, one or more contextual artificial intelligence datasets. The method further comprises updating, by the contextual intelligence system, the one or more contextual intelligent processes with at least one new service based on inputting the health triggering event, the event information, and the one or more contextual intelligent processes into the one or more contextual artificial intelligence datasets. The method further comprises performing, by the contextual intelligence system, the one or more updated contextual intelligent processes.

In other instances, the disclosure provides a contextual intelligence system. The contextual intelligence system includes a processor and non-transitory computer-readable medium having processor-executable instructions stored thereon. The processor-executable instructions, when executed, facilitate obtaining, from a user device, health information indicating a health triggering event associated with a user. The processor-executable instructions, when executed, further facilitate obtaining event information associated with the user. The processor-executable instructions, when executed, further facilitate determining, based on the health triggering event, one or more contextual intelligent processes for the health triggering event, wherein each of the one or more contextual intelligent processes comprises a sequence of actions, and wherein the sequence of actions comprises invoking a first service hosted on a first computing platform. The processor-executable instructions, when executed, further facilitate retrieving one or more contextual artificial intelligence datasets. The processor-executable instructions, when executed, further facilitate updating the one or more contextual intelligent processes with at least one new service based on inputting the health triggering event, the event information, and the one or more contextual intelligent processes into the one or more contextual artificial intelligence datasets. The processor-executable instructions, when executed, further facilitate performing the one or more updated contextual intelligent processes.

In yet other instances, the disclosure provides non-transitory computer-readable medium having processor-executable instructions stored thereon. The processor-executable instructions, when executed, facilitate obtaining, from a user device, health information indicating a health triggering event associated with a user. The processor-executable instructions, when executed, further facilitate obtaining event information associated with the user. The processor-executable instructions, when executed, further facilitate determining, based on the health triggering event, one or more contextual intelligent processes for the health triggering event, wherein each of the one or more contextual intelligent processes comprises a sequence of actions, and wherein the sequence of actions comprises invoking a first service hosted on a first computing platform. The processor-executable instructions, when executed, further facilitate retrieving one or more contextual artificial intelligence datasets. The processor-executable instructions, when executed, further facilitate updating the one or more contextual intelligent processes with at least one new service based on inputting the health triggering event, the event information, and the one or more contextual intelligent processes into the one or more contextual artificial intelligence datasets. The processor-executable instructions, when executed, further facilitate performing the one or more updated contextual intelligent processes.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIGS. 6a-6b are an exemplary updated contextual intelligent process in accordance with one or more exemplary embodiments of the present application.

FIG. 7 is an exemplary event sequence for managing and updating contextual intelligent processes using artificial intelligence algorithms in accordance with one or more exemplary embodiments of the present application.

DETAILED DESCRIPTION

Embodiments of the presented invention will now be described more fully hereinafter with reference to the accompanying FIGs., in which some, but not all, embodiments of the invention are shown. Indeed, the invention may be embodied in any different forms and should not be construed as limited to the embodiments set forth herein; rather, these embodiments are provided so that the disclosure will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Figure 1:
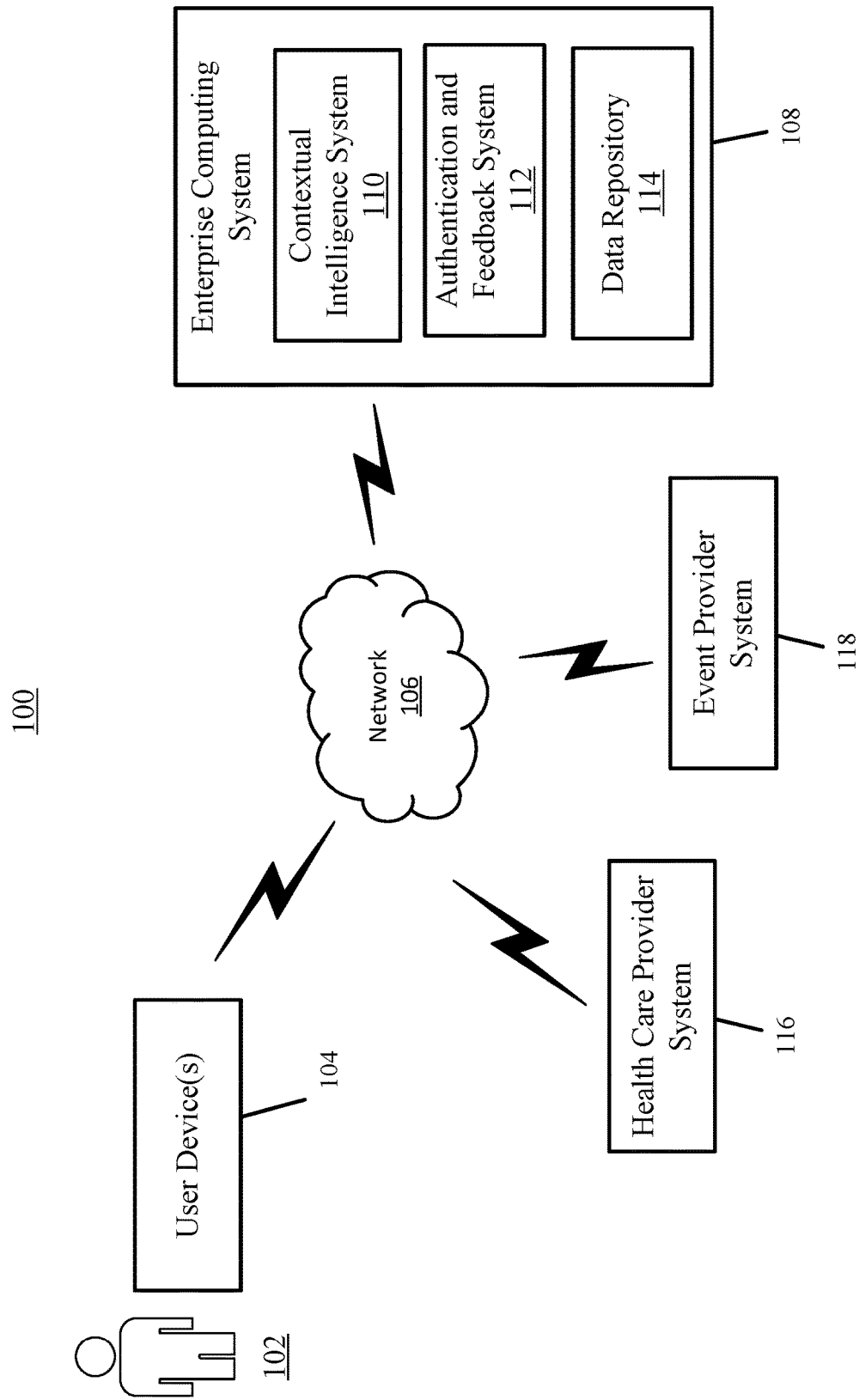
FIG. 1 is a simplified block diagram depicting an exemplary computing environment in accordance with one or more exemplary embodiments of the present application.

Systems, methods, and computer program products are herein disclosed that provide for managing and updating contextual intelligent processes using artificial intelligence algorithms FIG. 1 is a simplified block diagram depicting an exemplary environment in accordance with an exemplary embodiment of the present application. The environment 100 includes one or more user devices 104 associated with one or more users 102 and multiple systems and/or computing platforms including a healthcare provider system 116, an event provider system 118 and an enterprise computing system 108. As used herein, the systems and/or computing platforms within the environment 100 include one or more devices, servers, network elements, and/or other types of computing devices.

The systems and/or computing platforms within the environment 100 may be operatively coupled to (e.g., in communication with) other systems within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the systems and/or other components within the environment 100.

User 102 may be one or more users or members of an enterprise organization associated with the enterprise computing system 108. For example, the user 102 may communicate and/or provide medically relevant information to the enterprise organization using a user device 104. For example, the user device 104 may receive, determine, monitor, and/or otherwise obtain user information associated with the user. The user information may indicate a medically relevant event. The user device 104 may provide the user information to the enterprise computing system 108. The user device 104 may be and/or include, but are not limited to, a desktop, laptop, tablet, mobile device (e.g., smartphone device, or other mobile device), smart watch, an internet of things (IOT) device, or any other type of computing device that generally comprises one or more communication components, one or more processing components, and one or more memory components. The user device 104 may be able to execute software applications managed by, in communication, and/or otherwise associated with the enterprise organization.

The event provider system 118 may include one or more systems and/or computing platforms that provide event information to the enterprise computing system 108. The event information may indicate events such as weather events (e.g., severe weather), the medical history of the user, and any other type of events that may result in a status change for a medical claim associated with the user 102. In other words, the event provider system 118 may be and/or include a transaction system that processes medical claims for users such as the user 102. The event provider system 118 may receive, determine, and/or provide any type of events that results in a status change for a medical claim to the enterprise computing system 108. In some instances, the event provider system 118 may provide the event information to the enterprise computing system 108 automatically. In other instances, the event provider system 118 may provide the event information to the enterprise computing system 108 based on a request from the contextual intelligence system 110. The event provider system 118 may be and/or include, but are not limited to, one or more devices, computing platforms, servers, and/or other apparatuses capable of providing event information to the enterprise computing system 108.

The enterprise computing system 108 includes one or more computing devices, computing platforms, systems, servers, and/or other apparatuses capable of performing tasks, functions, and/or other actions for the enterprise organization. The enterprise organization may be any type of corporation, company, organization, and/or other institution. In some instances, the enterprise computing system 108 may, for example, receive user information from the user device 104, receive event information from an event provider system 118, manage and/or update one or more contextual intelligent processes, and provide the updated contextual intelligent processes to the health care provider system 116.

The enterprise computing system 108 includes a contextual intelligence system 110, an authentication and feedback system 112, and a data repository 114. The data repository 114 includes one or more processors and/or memory capable of storing information for the enterprise computing system 108. For example, the data repository 114 may include a database that stores contextual intelligent processes and/or artificial intelligence datasets (e.g., machine learning datasets and/or deep learning datasets). In some examples, the data repository 114 may include a big data database system having distributed storage across a plurality of computing nodes.

The contextual intelligence system 110 may manage and/or update the contextual intelligent processes based on the user information from the user device 104 and/or the event information from the event provider system 118. For example, the contextual intelligence system 110 may determine one or more contextual intelligent processes based on the user information and/or the event information. Contextual intelligent processes may include a sequence of actions, rules, steps, and/or other parameters for responding to the user information. For example, if the user is diabetic and the user information indicates the user's insulin level is outside of normal ranges, the contextual intelligence system 110 may determine one or more contextual intelligent processes to assist the diabetic user. The sequence of actions, rules, steps, and/or other parameters for the contextual intelligent processes may invoke and/or trigger one or more services (e.g., API calls) hosted by one or more health care provider (HCP) computing platforms (e.g., platforms within the health care provider (HCP) system 116). For instance, the HCP computing platform 116 may be a computing platform associated with a call-center or a computing platform associated with a prescription provider system that provides medical prescriptions for the user. Based on the user information and/or event information, the contextual intelligence system 110 may use artificial intelligence algorithms (e.g., machine learning algorithms and/or deep learning algorithms such as neural networks) to update the contextual intelligent processes in real-time and provide the updated contextual intelligent processes to the health care provider system 116. The contextual intelligence system 110 may store the updated contextual intelligent processes in the data repository 114.

The authentication and feedback (AF) system 112 may receive information used to update the artificial intelligence algorithms (e.g., datasets). For example, the AF system 112 may use information such as outputs (e.g., services/API calls) from the updated contextual intelligent processes to update the artificial intelligence datasets. In other words, after the contextual intelligence system 110 updates the contextual intelligent processes, the AF system 112 may determine the services from the contextual intelligent processes. The AF system 112 may compare the outputs (e.g., triggered services) with expected or predicted values (e.g., expected or predicted services). Based on the comparison, the AF system 112 may update the artificial intelligence datasets. For example, the artificial intelligence datasets may be neural networks with weights for each of the different levels (e.g., layers). The AF system 112 may use loss functions to update the weights of the neutral networks based on the comparison of the outputs (e.g., triggered services) with the expected or predicted services.

The contextual intelligence system 110 and/or the AF system 112 may be implemented using one or more computing platforms, devices, servers, and/or otherwise apparatuses that are capable of using artificial intelligence algorithms to manage and update contextual intelligent processes. In some variations, the contextual intelligence system 110 and/or the AF system 112 may be implemented as engines, software functions, and/or applications. In other words, the functionalities of the contextual intelligence system 110 and/or the AF system 112 might not be separate physical apparatuses, and may be implemented as software instructions stored in a storage (e.g., memory) and executed by one or more processors.

The HCP system 116 includes one or more service computing platforms, devices, and/or otherwise apparatuses that are capable of hosting services (e.g., applications) such as APIs, IBM INFORMATIONAL BUS (IIB), and so on. In other words and as used herein, a service may be any type of application, computer executable instructions and/or code that is capable of performing a particular function or operation. The services may be hosted on multiple different computing platforms that belong to different enterprise organizations and may be physically located in different geographical locations. As such, invoking or triggering a service may include invoking or calling a particular API, application, block of instructions, or block of code that may be hosted on different geographically located computing platforms. The HCP system 116 may include the multiple different computing platforms that manage and/or otherwise are associated with executing these services. Examples of these service computing platforms may include, but are not limited to, an emergency health care provider computing platform, a user-associated physician care computing platform, a prescription provider computing platform, and/or a call-center computing platform.

In some examples, the multiple different computing platforms within the HCP system 116 may belong to different enterprise organizations and/or be located in different geographical locations. For example, each enterprise organization may use different computing platforms (e.g., datacenters or servers) to host their services, and these computing platforms may be located at different geographical locations. In other examples, the HCP system 116 may be associated with the same enterprise organization as the enterprise computing system 108.

The emergency health care provider computing platform may host an emergency service such as an ambulance provider service (e.g., a service that provides a distress call for the user or an ambulance to a user), an emergency contact service (e.g., a service that contacts the user's emergency contacts), or emergency provider service (e.g., a service that contacts an emergency provider). When the emergency service is triggered, the emergency health care provider may conduct an emergency medical protocol for the user 102.

The user-associated physician care computing platform may host a physician service such as a service that determines the physician of the user 102 and provides a communication link between the user 102 and the physician. When the physician service is triggered, the service may permit the physician to be in communication (e.g., phone call, text alert, email alert, and/or other types of communication mediums) with the user 102.

The prescription provider computing platform may host a prescription service such as a service that provides medical prescriptions or drugs to the user. When the prescription service is triggered, the prescription service may determine a medical prescription (e.g., drug) for the user 102 and provide an alert of a physical location (e.g., pharmacy) where the user 102 may pick up the prescription.

The call-center computing platform may host a call-center service. When the call-center service is triggered, the call-center computing platform may display an alert on a computing device. A technician and/or automated call system from the call-center computing platform may make a call, provide an alert, and/or use another communication medium to contact the user 102 and check on the status of the user 102.

It will be appreciated that the exemplary environment depicted in FIG. 1 is merely an example, and that the principles discussed herein may also be applicable to other situations—for example, including other types of institutions, organizations, devices, systems, and network configurations. For example, in another configuration, the enterprise computing platform 108 may be separated into multiple different components that may communicate using the network 106. For instance, the contextual intelligence system 110 may be separated from the AF system 112 and communicate via the network 106. Additionally, and/or alternatively, one or more of the computing platforms included within the health care provider system 116 may be included within the enterprise computing system 108. For instance, the prescription provider computing platform may be included within the enterprise computing system 108.

As will be described below, the environment 100 may be used for health care services. However, in some variations, the environment 100 and the flowcharts, processes, event sequences, and/or other descriptions below may be used for other industries such as finance, manufacturing, and/or other services. In other words, the contextual intelligence system 110 may be used to update and/or manage contextual intelligent processes for these other industries.

Figure 2:
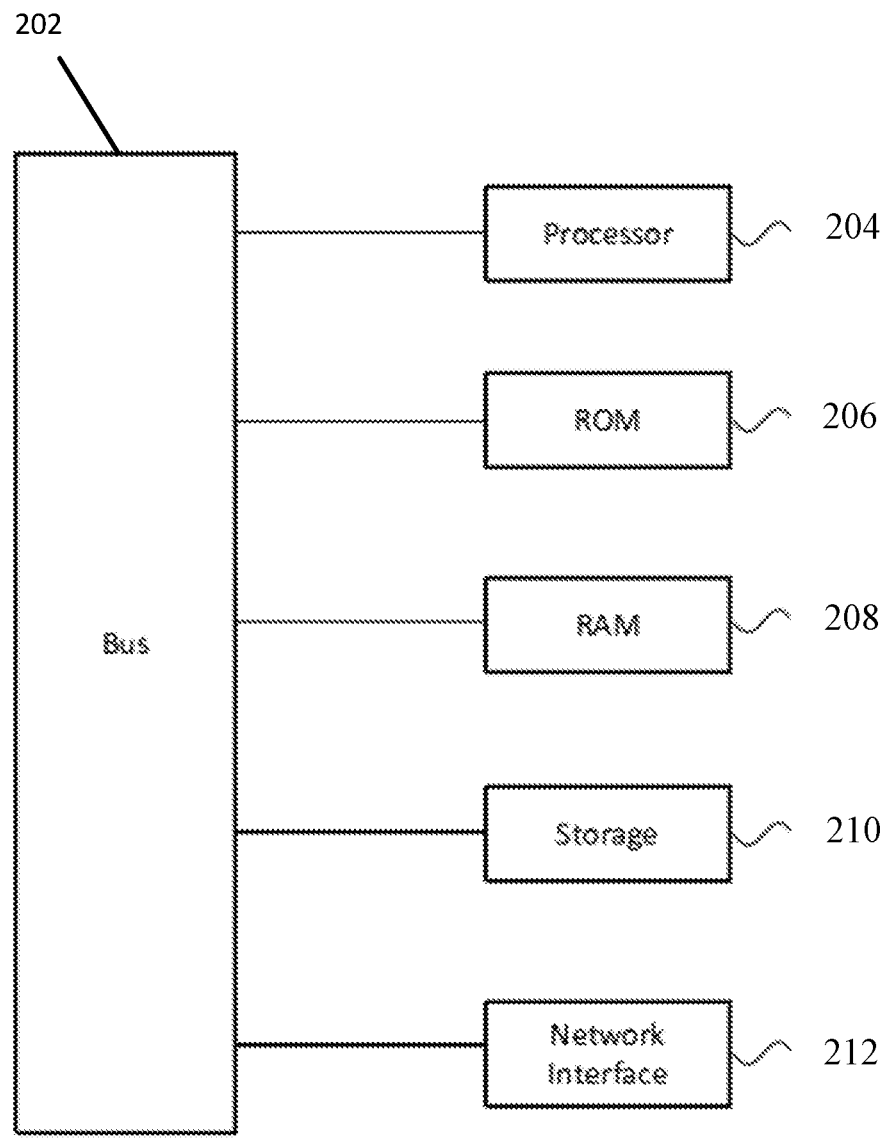
FIG. 2 is a simplified block diagram of one or more devices within the exemplary system of FIG. 1.

FIG. 2 is a block diagram of an exemplary system within the environment 100. The system 200 includes a processor 204, such as a central processing unit (CPU), controller, and/or logic, that executes computer executable instructions for performing the functions, processes, and/or methods described above. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The system 200 may also include a bus 202 that connects the processor 204, ROM 206, RAM 208, storage 210, and/or the network interface 212. The components within the system 200 may use the bus 202 to communicate with each other. The components within the system 200 might not be inclusive of every component, device, computing platform, and/or computing apparatus within the system 200. For example, the enterprise computing system 108 may include the components within system 200 and may also include the contextual intelligence system 110, the authentication feedback system 112, and/or the data repository 114. Additionally, and/or alternatively, each of the contextual intelligence system 110, the authentication feedback system 112, and/or the data repository 114 may include the components within the system 200. In other words, the contextual intelligence system 110, the authentication feedback system 112, and/or the data repository 114 may include a bus 202, one or more processors 204, ROM 206, RAM 208, storage 210, and/or a network interface 212.

The system of FIG. 2 may be used to implement the methods and systems described below. For example, the enterprise computing system 108 and/or the contextual intelligence system 110 may include one or more systems 200. Similarly, the other systems and/or devices (e.g., user device 104) may include one or more systems 200.

Figure 3:
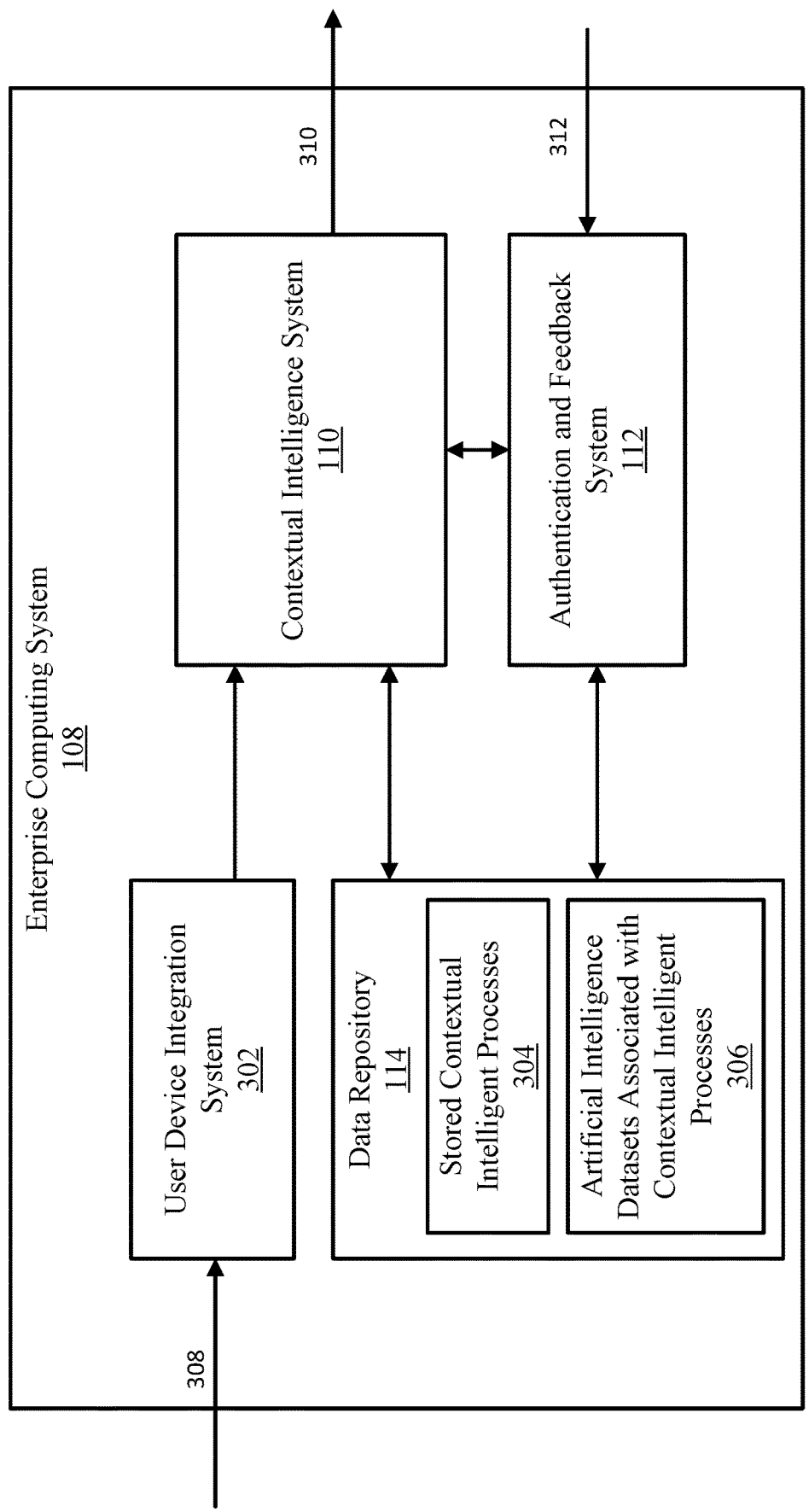
FIG. 3 is another simplified block diagram depicting an exemplary enterprise computing system in accordance with one or more exemplary embodiments of the present application.

FIG. 3 is another simplified block diagram depicting an exemplary enterprise computing system 108 in accordance with one or more exemplary embodiments of the present application. For example, the enterprise computing system 108 includes the contextual intelligence system 110, the AF system 112, and the data repository 114. Furthermore, the enterprise computing system 108 also includes a user device integration system 302. The user device integration system 302 may collect, monitor, and/or receive health information 308 from the user devices 104. The user device integration system 302 may also determine the intent of the information such as determining one or more categories (e.g., medical categories) associated with the information. The user device integration system 302 may provide the intent/medical categories associated with the information as well as the information from the user devices 104 to the contextual intelligence system 110. As will be described below, the health information 308 may include any type of medically relevant information such as heartrate of the user 102, insulin level of the user 102, age of the user 102, and/or any other information medically relevant to the user 102. In some variations, the functionalities of the user device integration system 302 may be included within the contextual intelligence system 108. For example, the contextual intelligence system 108 may receive the information from user device 104 and/or determine a medical category associated with the information.

The data repository 114 may include stored contextual intelligent processes 304 and artificial intelligence datasets associated with the contextual intelligent processes 306. For example, the contextual intelligent processes 304 may be a sequence of actions that invoke or trigger one or more services (e.g., API calls). The artificial intelligence datasets 306 may be machine learning datasets and/or deep learning (e.g., neural network) datasets used to update the contextual intelligent processes 306. For instance, based on the information from the user devices 104, the contextual intelligence system 110 may determine and/or obtain (e.g., receive and/or retrieve) one or more stored contextual intelligent processes 304 and one or more artificial intelligence datasets 306 from the data repository 114. The contextual intelligence system 110 may use the artificial intelligence datasets 306 to generate new or updated contextual intelligent processes 304. The new or updated contextual intelligent processes 304 may include a different sequence of actions such as including triggering one or more new services (e.g., new API calls), replacing one or more services (e.g., replacing a previous API call from the retrieved contextual intelligent process 304 with a new API call), and/or removing one or more services (e.g., removing a previous API call from the retrieved contextual intelligent process 304).

The contextual intelligence system 110 may provide information 310 to the HCP system 116. The information 310 may include the new and/or updated contextual intelligent processes and/or one or more instructions directing the HCP system 116 to implement the new and/or updated contextual intelligent processes.

The AF system 112 may also receive the outputs from the artificial intelligence datasets 306. In other words, the AF system 112 may receive the generated new or updated contextual intelligent processes 304 and determine the services to be triggered or invoked within these processes 304. The AF system 112 may compare these services with expected or predicted services and update the artificial intelligence datasets 306 based on the comparison. For example, the artificial intelligence datasets 306 may be a neural network with a plurality of weights. The AF system 112 may use one or more loss functions and the comparisons to update the weights within the neural network. The AF system 112 may then store the updated artificial intelligence datasets 306 within the data repository 114. Then, in the next iteration, the contextual intelligence system 110 may use the updated artificial intelligence datasets 306 to generate new and/or updated contextual intelligent processes 304 and provide these processes 304 to the HCP system 116.

Additionally, and/or alternatively, the AF system 112 may receive information 312 from the HCP system 116 and use the information 312 to update the artificial intelligence datasets. For example, the HCP system 116 may provide feedback information indicating feedback of using the new and/or updated contextual intelligent processes 304. The HCP system 116 may update the artificial intelligence datasets 306 based on the feedback information. The descriptions, illustrations, and processes of FIG. 3 are merely exemplary and the enterprise computing system 108 may use other descriptions, illustrations, and processes to manage and update contextual intelligent processes using artificial intelligence algorithms.

Figure 4:
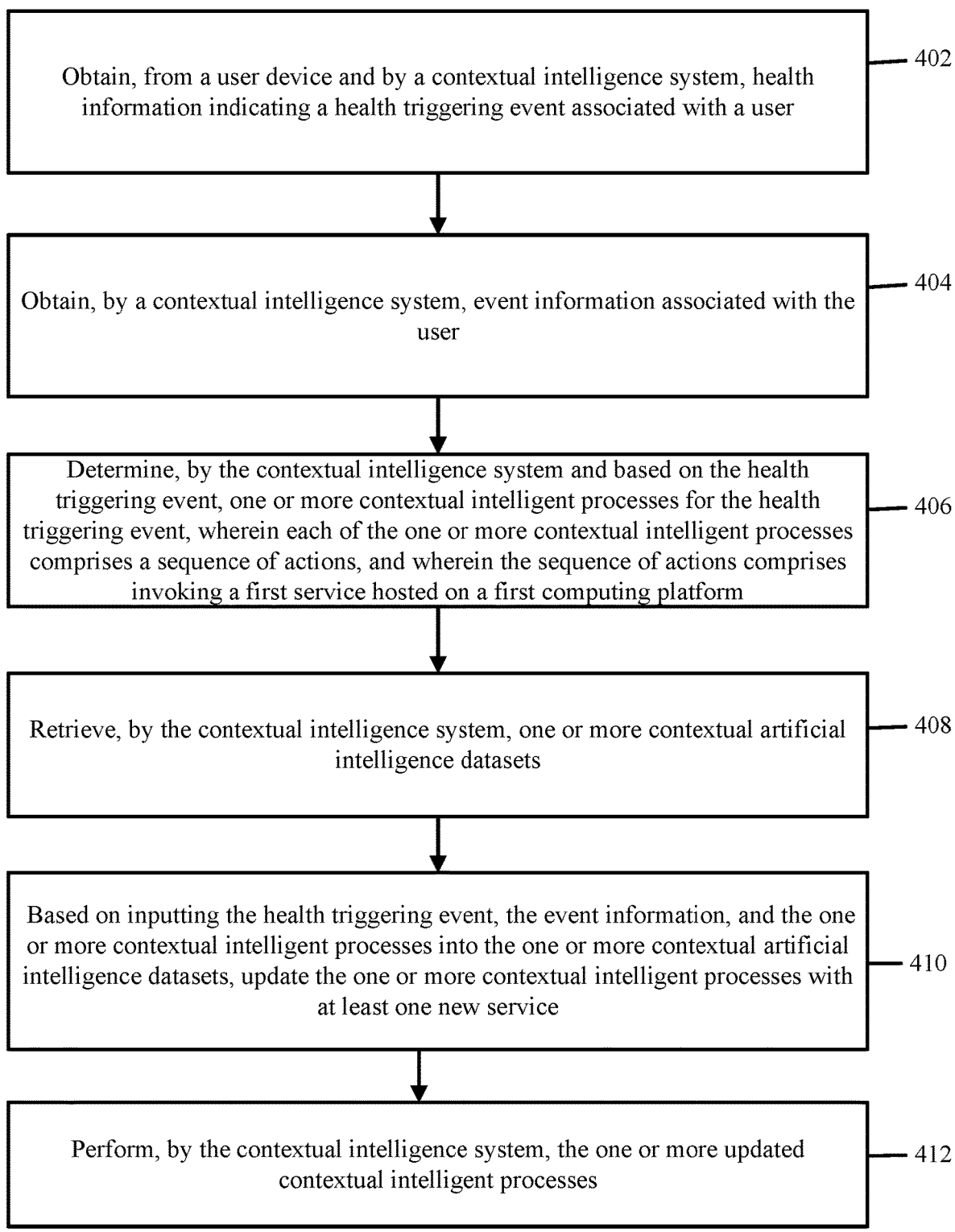
FIG. 4 is an exemplary flowchart for managing and updating contextual intelligent processes using artificial intelligence algorithms in accordance with one or more exemplary embodiments of the present application.

FIG. 4 is an exemplary flowchart 400 for managing and updating contextual intelligent processes using artificial intelligence algorithms in accordance with one or more exemplary embodiments of the present application. The flowchart 400 may be performed by the enterprise computing system 108 shown in FIGS. 1 and 3 and in particular the contextual intelligence system 110 from these FIGs.; however, it will be recognized that any suitable environment may be used to perform flowchart 400 and that any of the following blocks may be performed in any suitable order. The descriptions, illustrations, and processes of FIG. 4 are merely exemplary and the process 400 may use other descriptions, illustrations, and processes to manage and update contextual intelligent processes using artificial intelligence algorithms.

At block 402, the contextual intelligence system 110 obtains, from the user device 104, health information 308 indicating a health triggering event associated with the user 102. For example, the user device integration system 302 may receive health information 308 from the user device 104. The user device integration system 302 may determine one or more medical categories based on the health information 308 and provide the health information 308 and/or the medical categories to the contextual intelligence system 110. The health information 308 may indicate health parameters or characteristics associated with the user 102 and may be monitored by the user device 104. For example, the health parameters and/or characteristics may include, but are not limited to, heart rate of the user 102, member age of the user, and/or insulin level of the user 102. For instance, the user device 104 may be a smart phone or wearable device that includes one or more sensors. The user device 104 may monitor characteristics, such as heart rate and/or insulin level of the user 102, and provide the characteristics to the contextual intelligence system 110. In some examples, the contextual intelligence system 110 includes the functionality of the user device integration system 302. In other words, the contextual intelligence system 110 receives the health information 308 and determines the medical categories associated with the health information 308.

Based on the determined medical category, the contextual intelligence system 110 may determine a health triggering event associated with the user 102. In some examples, the health information 308 may include an insulin level of the user 102 and the contextual intelligence system 110 may determine whether the insulin level of the user 102 exceeds an insulin threshold. Based on the insulin level exceeding the threshold, the contextual intelligence system 110 may determine that the health information 308 indicates a health triggering event. In other words, the contextual intelligence system 110 compares health parameters or characteristics from the health information 308 with thresholds and determines health triggering events based on the comparison. In some instances, the contextual intelligence system 110 may determine the threshold based on the one or more medical categories (e.g., if the medical category is insulin or diabetic, the contextual intelligence system 110 may use the medical category to determine an insulin threshold). In some variations, the user device integration system 302 may determine the health triggering event and provide it to the contextual intelligence system 110.

At block 404, the contextual intelligence system 110 obtains, from the event provider system 118, event information associated with the user 102. As described above, the event information may indicate events such as weather events (e.g., severe weather), events within the medical history of the user, and any other type of events that may result in a status change for a medical claim associated with the user 102.

At block 406, the contextual intelligence system 110 determines one or more contextual intelligent processes for the health triggering event based on the health triggering event and/or the event information. For example, as described above, contextual intelligent processes may include a sequence of actions and the sequence of actions includes triggering (e.g., invoking) one or more services hosted on service computing platforms of the HCP system 116. For instance, the service computing platforms may belong to different enterprise organizations and may host multiple different services. The contextual intelligent processes may indicate for a system such as the enterprise computing system 108 and/or the HCP system 116 to trigger services (e.g., APIs) hosted on one or more computing platforms (e.g., the service computing platforms from the HCP system 116) to invoke (e.g., call or trigger). The contextual intelligent processes may be stored in the data repository 114. After determining the contextual intelligent processes, the contextual intelligence system 110 may retrieve the stored contextual intelligent processes 304 from the data repository 114.

Each contextual intelligent processes may be associated with health triggering event, characteristic and/or parameter from the health information 308, and/or determined medical category. For example, the data repository 114 may include one or more stored contextual intelligent processes 304 for a heart rate of the user 102 and one or more separate contextual intelligent processes 304 for an insulin level the user 102. Additionally, and/or alternatively, the data repository 114 may include one or more stored contextual intelligent processes 304 that are for both the heart rate and insulin level.

Figure 5:
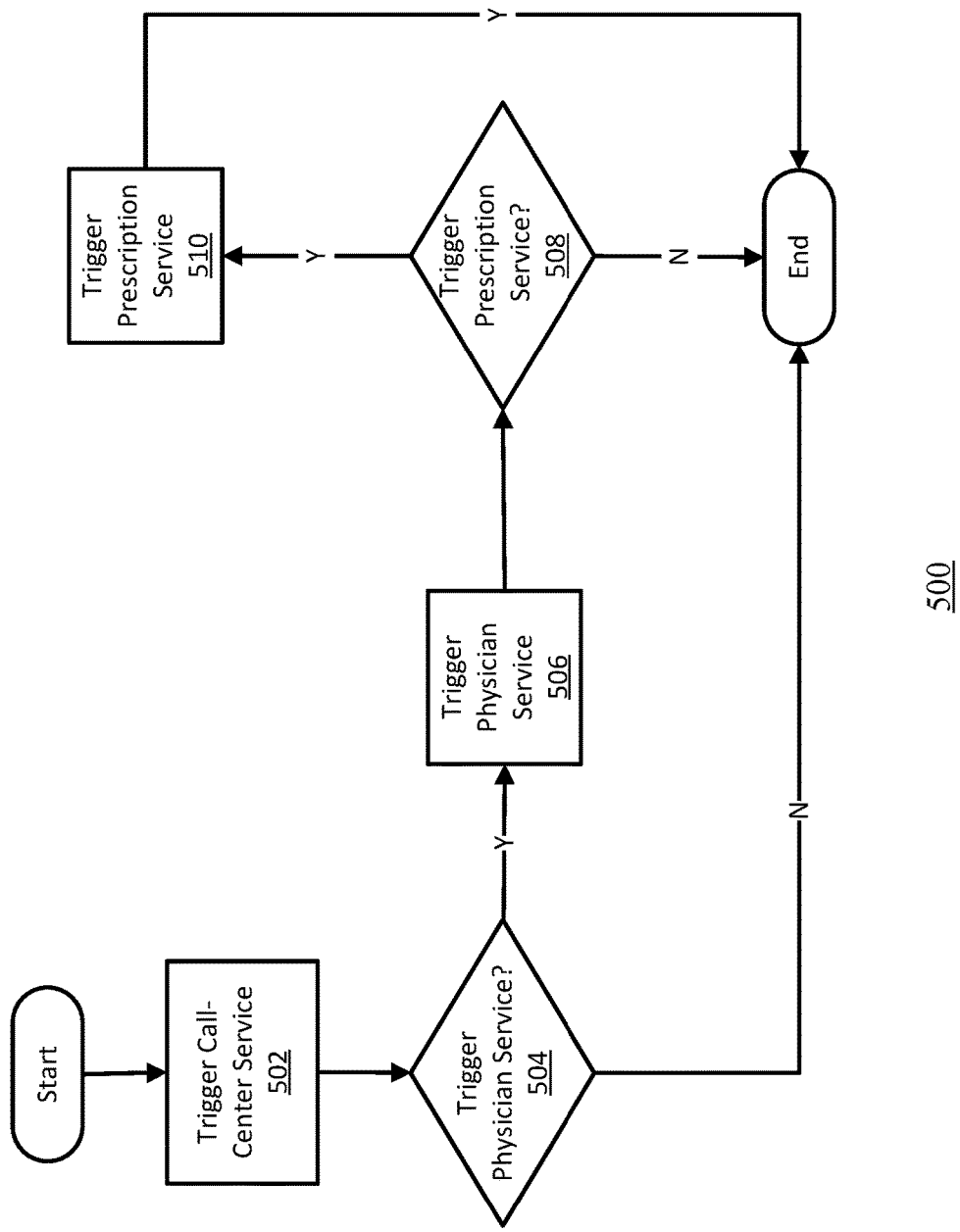
FIG. 5 is an exemplary contextual intelligent process in accordance with one or more exemplary embodiments of the present application.

FIG. 5 shows an exemplary contextual intelligent process 500 in accordance with one or more exemplary embodiments of the present application. However, the contextual intelligent process 500 is merely an example and other types of contextual intelligent processes are contemplated herein. In other words, contextual intelligent processes may include any number of services (e.g., API calls) being hosted by one or more service computing platforms within the HCP system 116 and the contextual intelligent process 500 may be only one non-limiting example of these contextual intelligent processes.

Referring to FIG. 5, the contextual intelligence system 110 may retrieve the stored contextual intelligent process 500 from the data repository 114 based on the health information and/or the event information. For instance, the health information may indicate an insulin level and a heart rate of the user 102. The contextual intelligence system 110 may determine a health triggering event associated with the insulin level and/or the heart rate. Then, based on these factors, the contextual intelligence system 110 may retrieve the contextual intelligent process 500 from the data repository 114 based on the health information and the health triggering event.

The contextual intelligent process 500 may indicate a plurality of services that may be hosted on different computing platforms for different enterprise organizations. For example, as mentioned above, the physician service (e.g., physician API) may be hosted on a computing platform that might be different from the call-center service's computing platform. In other words, one enterprise organization may operate and/or manage the enterprise computing system 108 and the computing platform that hosts the call-center service. Accordingly, each enterprise organization may have their own datacenters and/or servers that host their own services.

The contextual intelligent process 500 may include a sequence of actions including a block 502 to trigger a call-center service 502. In operation, block 502 may invoke or trigger the call-center service. For example, a system (e.g., the enterprise computing system 108 and/or another system) may direct a call-center computing platform from the HCP system 116 to place a call, alert, or otherwise attempt to communicate with the user 102 to check on the user 102. For instance, if the user device 104 indicates the insulin level of the user 102 is too high, the call-center computing platform may attempt to contact the user 102 (e.g., by providing an alert to a call-center employee to place a call to the user 102 and/or by automating a call to the user 102).

The sequence of actions from process 500 may further include a block 504 that determines whether to trigger a physician service. For example, based on the call-center service (e.g., based on the call-center's communication with the user 102), the system may determine whether to trigger a physician service. In other words, if the call-center service is unable to contact the user 102 or the user 102 indicates they would like to seek physician service, then the enterprise system 108 may determine to move to block 506 and trigger a physician service. If the user 102 indicates they would not like to seek physician service, then the process may end. The computing platform hosting the physician service may be the same computing platform or a different computing platform from the computing platform hosting the call-center service.

The sequence of actions from process 500 may further include a block 506 that triggers a physician service. For example, by invoking or triggering the physician service, the system may direct a physician computing platform within the HCP system 116 to determine a primary care physician (PCP) for the user 102 (e.g., based on the event information indicating medical records for the user 102) and inform the PCP for the user 102 of the health triggering event (e.g., the insulin level of the user 102 exceeds a threshold). Additionally, and/or alternatively, block 506 may also be used to update the medical records for the user 102 and/or provide reminders to the PCP for follow-up care.

The sequence of actions from process 500 may further include a block 508 that determines whether to trigger a prescription service. For example, based on the physician service (e.g., based on the physician's communication with the user 102), the system may determine whether to trigger a prescription service. In other words, if the physician service is unable to contact the user 102 or if the user's 102 physician indicates the user 102 requires a new prescription or an updated prescription, then the enterprise system 108 may determine to move to block 510 and trigger a prescription service. Otherwise, the contextual intelligent process 500 may end.

The sequence of actions from process 500 may further include a block 510 that triggers the prescription service. For example, by invoking or triggering the prescription service, the system may direct a prescription computing platform within the HCP system 116 to provide and/or update a prescription for the user. Additionally, and/or alternatively, the prescription service may direct the prescription computing platform to provide a prescription location to the user 102 so the user 102 may pick up the prescription.

As mentioned above, the contextual intelligent process 500 is merely an example of a stored contextual intelligent process 304 from the data repository 114. The data repository 114 may include numerous other contextual intelligent processes 304 that are directed towards different health parameters, characteristics, health triggering events, and/or event information. In some instances, the AF system 112 or another device may provide the initial iterations of the contextual intelligent processes 304 with the services (e.g., APIs). In other instances, the contextual intelligence system 108 may use artificial intelligence such as deep learning to determine the initial iterations of the contextual intelligent processes 304 and store these processes in the data repository 114. In either of these instances and as will be described below, the contextual intelligence system 108 may manage and update these contextual intelligent processes 304.

Referring back to FIG. 4, at block 408, the contextual intelligence system 108 may retrieve one or more contextual artificial intelligence datasets 306 from the data repository 114. The contextual artificial intelligence datasets 306 may be any type of artificial intelligence datasets including machine learning datasets and/or deep learning datasets. For example, the contextual artificial intelligence datasets 306 may be a neural network that includes a plurality of weights associated with different layers.

In some instances, the contextual artificial intelligence datasets 306 may be associated with individual contextual intelligent processes 304. For example, the contextual intelligent process 500 shown on FIG. 5 may have a particular artificial intelligence dataset 306. Based on retrieving the contextual intelligent process 500, the contextual intelligence system 108 may retrieve the artificial intelligence dataset 306 that is associated with the contextual intelligent process 500. In other instances, the contextual artificial intelligence datasets 306 may be associated with a number of different contextual intelligent processes 500.

At block 410, the contextual intelligence system 110 updates the one or more contextual intelligent processes based on inputting the health information 308, the health triggering event, the event information, and/or the one or more determined contextual intelligent processes into one or more contextual artificial intelligence datasets. For example, the contextual intelligence system 110 may use the health triggering event, the event information, the health information 308 from the user device 104, and/or the determined contextual intelligent processes from block 406 as inputs into the contextual artificial intelligence datasets 306. Then, based on inputting the inputs into the contextual artificial intelligence datasets 306, the contextual intelligence system 110 may determine one or more new and/or updated contextual intelligent processes. The one or more new and/or updated contextual intelligent processes may include a sequence of actions that removes one or more services from the previous iteration of the contextual intelligent processes, replaces one or more services from the previous iteration of the contextual intelligent processes with one or more new services, and/or adds one or more new services into the previous iteration of the contextual intelligent processes.

Figure 6A:
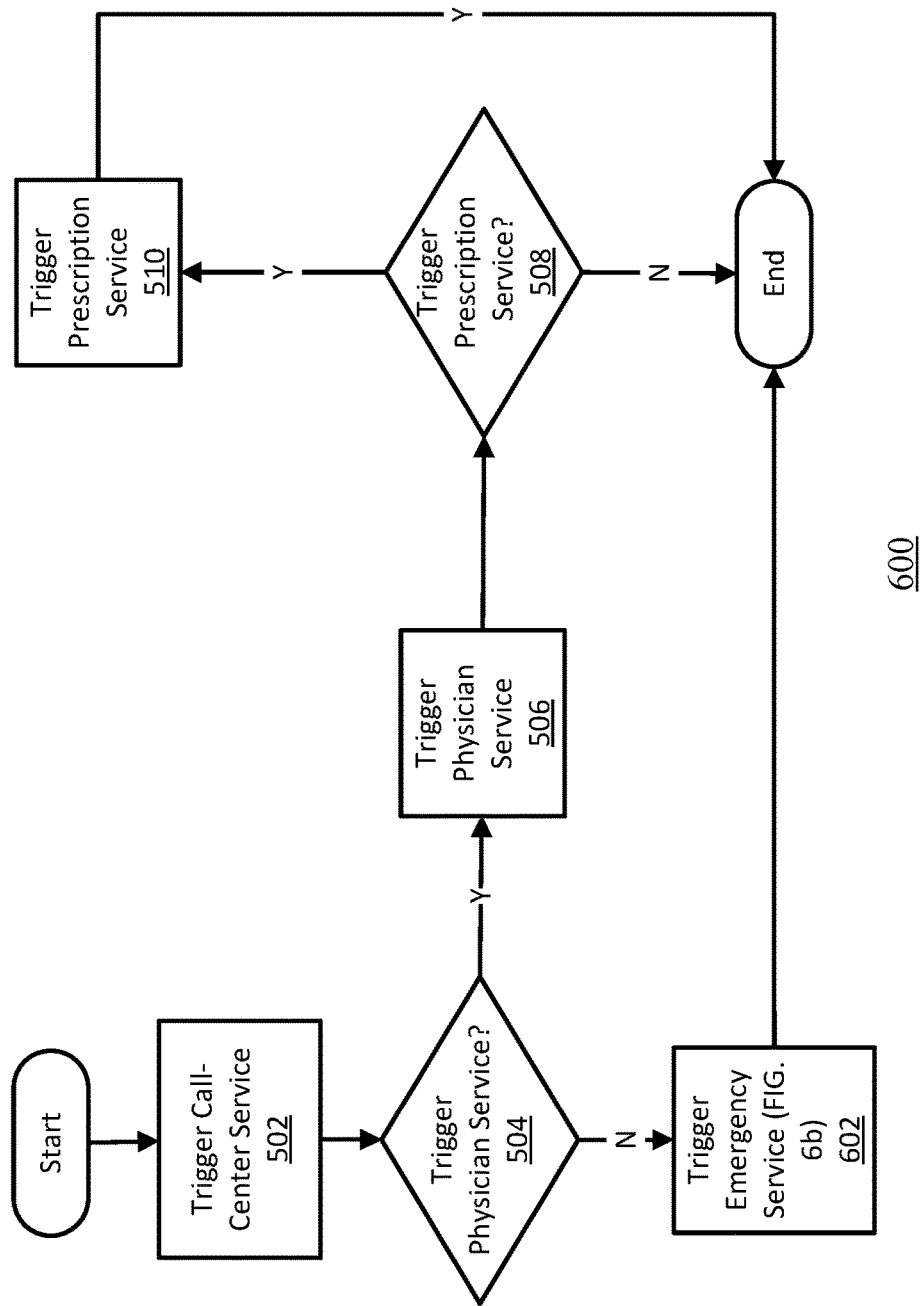

FIGS. 6a and 6b show an updated contextual intelligent process 600. For example, the contextual intelligence system 110 may input the health information 308, the health triggering event, the event information, and the contextual intelligent process 500 into one or more retrieved contextual artificial intelligence datasets from block 408 to generate the updated contextual intelligent process 600 shown in FIGS. 6a and 6b. However, similar to the contextual intelligent process 500, the updated contextual intelligent process 600 is merely exemplary and the contextual intelligence system 110 may update different contextual intelligent processes stored in the data repository 114 and may update the contextual intelligent process 500 different from the example shown in FIGS. 6a and 6b.

Using the retrieved contextual artificial intelligence datasets from block 408, the contextual intelligence system 110 includes at least one change to the contextual intelligent process 500 to generate the updated contextual intelligent process 600. For instance, the at least one change may include adding one or more new services into the previous iteration of the contextual intelligent processes. As mentioned before, the contextual intelligent process 600 generated using the health information, the event information, and the retrieved contextual intelligent process 500 may be exemplary and based on the above inputs, the contextual intelligence system 110 may generate different updated contextual intelligent processes. For instance, in other iterations, the contextual intelligence system 100 may generate updated contextual intelligent processes using the contextual artificial intelligence datasets such as by removing one or more services from the retrieved contextual intelligent process 500, replacing one or more services from the retrieved contextual intelligent process 500 with one or more new services, and/or adding different services to the contextual intelligent process 500.

Referring to FIG. 6a, in some examples, the event information may have indicated a severe weather event. The contextual intelligence system 110 may use the retrieve contextual artificial intelligence datasets to generate the updated contextual intelligent process 600 using the event information (e.g., the severe weather event) and the contextual intelligent process 500. For instance, referring to blocks 502 and 504 from the process 500 and 600, a system may have triggered the call-center service and might not have received confirmation from the user 102. For the contextual intelligent process 500, if the call-center service is unable to contact the user 102, then the enterprise system 108 may determine to move to block 506 and trigger a physician service. However, in contextual intelligent process 600, if the call-center service is unable to contact the user 102, then the enterprise system 108 may determine to move to block 602 and trigger emergency service 602. In other words, the event information (e.g., severe weather event) may have caused the contextual artificial intelligence dataset to output a contextual intelligent process 600 that increases the severity of the user not responding the confirmation and as such, trigger the emergency service.

Additionally, and/or alternatively, the health information 308 and/or the health triggering event may also cause the contextual intelligence system 110 to generate the updated contextual intelligent process 600. For example, the health information 308 may indicate an insulin level of the user 102. If the insulin level of the user 102 is significantly over the threshold, the contextual intelligence system 110 may generate the updated contextual intelligent process 600 using the health triggering event/health information 308 and the contextual intelligent process 500. In other words, the contextual intelligence system 110 may update the contextual intelligent process 500 with block 602. For example, in contextual intelligent process 600, if the call-center service is unable to contact the user 102, then the enterprise system 108 may determine to move to block 602 and trigger emergency service 602.

FIG. 6b describes triggering the emergency service 602 in more detail. However, the emergency service 602 shown in FIG. 6b is merely exemplary and in other examples, different and/or additional blocks may be used. The emergency service 602 may include triggering multiple different services hosted on different computing platforms.

In operation, the sequence of actions for the emergency service 602 may include triggering an emergency health care provider service 610. For example, by triggering the emergency health care provider service, the system may first determine an emergency provider (e.g., hospital, urgent care center, and/or other type of emergency health provider) that is in close proximity to the user 102. Additionally, and/or alternatively, the event information (e.g., medical records for the user 102) may provide the preferred emergency provider (e.g., hospital) for the user 102. The system may then notify the user 102 of the emergency provider location and notify the emergency provider to prepare the user 102 for admission. In some examples, the patient has been admitted, the system may receive an indication that the patient has been admitted to the emergency provider location.

Further, the sequence of actions for the emergency service 602 may include triggering an emergency contact service 612. For example, by triggering the emergency contact service 612, the system may determine if the user 102 has an emergency contact (e.g., by reviewing the event information such as the medical records of the user 102) and the identity of the emergency contact. Then, the system may notify the emergency contact of the user's 102 condition and notify the location of the emergency provider. The sequence of actions for the emergency service 602 shows the trigger emergency health care provider service 610 and the trigger emergency contact service 612 as being performed sequentially. However, in other instances, these two services 610 and 612 may be performed in parallel. In other words, the two services 610 and 612 may be performed in substantially real-time of each other such that the emergency contacts may be notified at substantially real-time of when the emergency providers are notified.

The sequence of actions for the emergency service 602 may also include triggering a physician service 614. For example, by triggering the physician service 614, the system may determine the PCP of the user 102 and inform the PCP of the user 102 of the situation (e.g., the user 102 has been admitted to the hospital). Additionally, and/or alternatively, block 614 may be used to update the medical records for the user 102 and/or provide reminders to the PCP for follow-up care. After, the contextual intelligent process 600 may move back to FIG. 6a and end.

Referring back to FIG. 4, at block 412, the contextual intelligence system 110 performs the updated contextual intelligent processes. For example, the contextual intelligence system 110 may direct a system (e.g., another system within the enterprise computing system 108 and/or the HCP system 116) to perform the updated contextual intelligent processes such as the updated contextual intelligent process 600. By performing and/or directing another system to perform the updated contextual intelligent processes, the contextual intelligence system 110 may cause the services within the updated contextual intelligent process (e.g., the services within the contextual intelligent process 600 such as the call-center service 502, physician service 506, prescription service 508, and/or the emergency service 602) to be triggered. In other words, the contextual intelligence system 110 may trigger one or more API calls and/or direct other systems to trigger the one or more API calls to be triggered.

Additionally, and/or alternatively, after performing the contextual intelligent processes, the contextual intelligence system 110 may store the updated contextual intelligent processes in the data repository 114 and the flowchart 400 may repeat continuously. As such, in the next iteration such as after receiving new event information, receiving new health information 308, and/or determining new health triggering events, the contextual intelligence system 110 may perform flowchart 400 again. In other words, the contextual intelligence system 110 may input new information (e.g., new event information, new health information, and/or new health triggering events) and the updated contextual intelligent processes (e.g., contextual intelligent process 600) into the artificial intelligence datasets to generate another updated contextual intelligent process. The contextual intelligence system 110 may then perform the updated contextual intelligent processes.

Additionally, and/or alternatively, the contextual intelligence system 110 and/or the authentication and feedback system 112 may continuously the one or more contextual artificial intelligence datasets. For instance, the contextual intelligence system 110 and/or the authentication and feedback system 112 may update the artificial intelligence datasets 306 stored in the data repository 114. The contextual intelligence system 110 and/or the authentication and feedback system 112 may update the artificial intelligence datasets 306 based on comparing the output of the artificial intelligence datasets 306 with the expected or predicted outputs. For example, as described above, the outputs of the artificial intelligence datasets 306 may include a new and/or updated contextual intelligent processes that comprises a sequence of actions including the services (e.g., APIs) being hosted on different computing platforms of the HCP system 116. The authentication and feedback system 112 may receive the expected or predicted outputs (e.g., expected or predicted services/APIs) and update the contextual artificial intelligence datasets based on the comparison.

In some examples, the contextual artificial intelligence dataset is a deep learning (e.g., neural network) dataset. The authentication and feedback system 112 may update the weights within the neural network based on the comparison and using one or more loss functions. The one or more loss functions are optimization functions of machine learning and/or deep learning algorithms and the authentication and feedback system 112 may update the contextual artificial intelligence datasets based on these loss functions. For instance, the authentication and feedback system 112 may determine expected or predicted outputs to not include an emergency service 602. For example, in severe weather events, if the call-center service 502 is unable to get into contact with the user 102, the expected output should be to notify the emergency contact service 612, but not to trigger emergency health care provider service 610. In other words, the emergency contact may know how to get into contact with the user 102 and the user 102 might not need to go to a hospital. As such, the authentication and feedback system 112 may update the weights within the neural network using loss functions so that the emergency health care provider service 610 is not triggered for those events. Then, the authentication and feedback system 112 may store the updated artificial intelligence datasets (e.g., updated weights) within the data repository 114. In the next iteration of flowchart 400, the contextual intelligence system 108 may use the updated artificial intelligence datasets to generate the new and/or updated contextual intelligent processes.

Additionally, and/or alternatively, the authentication and feedback system 112 may update the artificial intelligence datasets 306 using supervised and/or unsupervised learning. For example, an operator of the authentication and feedback system 112 may review the output (e.g., services/APIs) from the artificial intelligence datasets and provide information to update the artificial intelligence datasets 306 based on the output from the artificial intelligence datasets and the expected resultant outputs (e.g., expected services/APIs). In the next iteration of flowchart 400, the contextual intelligence system 108 may use the updated artificial intelligence datasets to generate the new and/or updated contextual intelligent processes.

In some instances, based on the health information 308 and/or the event information, the contextual intelligence system 110 may update more than one contextual intelligent process and then aggregate these contextual intelligent processes. For example, the health information 308 may indicate parameters and/or characteristics that are associated with multiple contextual intelligent processes. The contextual intelligence system 110 may retrieve these contextual intelligent processes from the data repository 114, update these processes using artificial intelligence datasets (e.g., a single artificial intelligence dataset and/or more than one artificial intelligence dataset associated with the multiple contextual intelligent processes), aggregate the updated contextual intelligent processes, and then perform the aggregated processes. FIG. 7 shows an exemplary event sequence 700 for managing and updating contextual intelligent processes using artificial intelligence algorithms and will be used to describe aggregating the contextual intelligent processes in more detail. However, the event sequence 700 is merely an example and other types of event sequences are contemplated herein.

At block 702, the user device(s) 104 may provide health information (e.g., heart rate, member age, insulin level) to the contextual intelligence system 110. At block 704, the contextual intelligence system 110 may obtain event information such as from the event provider system 118.

At block 704, the contextual intelligence system 110 may retrieve more than one contextual intelligent process from the data repository 114. For example, the contextual intelligence system 110 may retrieve three contextual intelligent processes—a medical history detection process based on the member age, a heartrate abnormality process based on the heart rate of the user 102, and an insulin abnormality process based on an insulin level of the user 102. Further, the contextual intelligence system 110 may retrieve one or more artificial intelligence (AI) datasets from the data repository 114. In some examples, the contextual intelligence system 110 may retrieve a single AI dataset for all three processes. In other examples, the contextual intelligence system 110 may retrieve an AI dataset for one of the processes (e.g., medical history detection process) and another AI dataset for the other two processes (e.g., heartrate abnormality and insulin abnormality processes). In yet other examples, the contextual intelligence system 110 may retrieve different AI datasets for each of the processes.

At block 708, the contextual intelligence system 110 may update the contextual intelligence processes using the AI datasets as described above. Then, the contextual intelligence system 110 may aggregate the updated processes. For instance, each of these processes may include a sequence of actions with one or more services. The contextual intelligence system 110 may aggregate the sequence of actions for the updated contextual intelligence processes including having a single sequence of actions with all of the services from the individual processes.

At block 710, the contextual intelligence system 110 may perform the aggregated processes.

In some variations, the contextual intelligence system 110, the flowchart 400, and/or the event sequence 700 may use artificial intelligence such as deep learning for various different applications. For example, the contextual intelligence system 110 may perform the flowchart 400 and/or the event sequence 700 to improve the health of the user 102 and/or motivate the user to be more health conscious. For example, the contextual intelligence system 110 may collect health information related to the user 102. The contextual intelligence system 110 may then use the flowchart 400 and/or the event sequence 700 to determine patterns and predict associations to improve the health of the user 102 (e.g., indicating to the user 102 that diet may improve the glucose levels and exercise results may impact the heart rate). Furthermore, the contextual intelligence system 110 may use loss functions to provide further insights on the correlations.

In other variations, the contextual intelligence system 110, the flowchart 400, and/or the event sequence 700 may use deep learning for other applications such as computer vision and retina scan. For instance, the contextual intelligence system 110 may perform the flowchart 400 and/or the event sequence 700 (e.g., using AI datasets such as deep learning) by using a computing vision application to take skin tests for the user 102 and inform the user 102 of an underlying condition. Additionally, and/or alternatively, the contextual intelligence system 110 may perform the flowchart 400 and/or the event sequence 700 (e.g., using AI datasets such as deep learning) by using a retina scan application to understand the overall health of a user's eye.

It will be appreciated that the figures of the present application and their corresponding descriptions are merely exemplary, and that the invention is not limited to these exemplary situations.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the embodiments of the invention described herein are merely exemplary. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method, comprising:
obtaining, from a user device and by a contextual intelligence system, health information comprising a heart rate of a user and an insulin level of the user;
determining, by the contextual intelligence system, a plurality of health triggering events based on comparing the heart rate of the user with one or more first thresholds and the insulin level of the user with one or more second thresholds;
obtaining, by the contextual intelligence system, event information associated with the user;
determining, by the contextual intelligence system and based on the plurality of health triggering events, a plurality of contextual intelligent processes, wherein the plurality of contextual intelligent processes comprises a heart rate abnormality process associated with the heart rate of the user and an insulin abnormality process associated with the insulin level of the user, wherein each of the plurality of contextual intelligent processes comprises a sequence of actions, and wherein the sequence of actions comprises invoking a first service indicating a first application programming interface (API) hosted on a first computing platform and a determination of whether to trigger a physician service;
retrieving, by the contextual intelligence system, one or more contextual artificial intelligence algorithms;
inputting, by the contextual intelligent system, the plurality of health triggering events, the event information, and each of the plurality of contextual intelligent processes into the one or more contextual artificial intelligence algorithms to generate a plurality of updated contextual intelligent processes, wherein the plurality of updated contextual intelligent processes comprises an updated heart rate abnormality process and an updated insulin abnormality process;

aggregating, by the contextual intelligent system, the plurality of updated contextual intelligent processes into an aggregated updated contextual intelligent process comprising a single sequence of actions, wherein the aggregated updated contextual intelligent process comprises at least one new service indicating a second API hosted on a second computing platform that is different from the first computing platform, wherein the at least one new service comprises triggering an emergency service based on the determination of whether to trigger the physician service; and performing, by the contextual intelligence system, the aggregated updated contextual intelligent process, wherein performing the aggregated updated contextual intelligent process comprises invoking the second API hosted on the second computing platform to trigger the emergency service, wherein triggering the emergency service comprises triggering an emergency health care provider service, and wherein triggering the emergency health care provider service comprises invoking the second API hosted on the second computing platform to notify an emergency provider to prepare the user for admission to the emergency provider.

2. The method of claim 1, wherein the second API replaces the first API within the aggregated updated contextual intelligent process.

3. The method of claim 1, wherein the at least one new service is sequentially placed after the first service within the aggregated updated contextual intelligent process.

4. The method of claim 1, wherein the aggregated updated contextual intelligent process removes a third API from the sequence of actions of the heart rate abnormality process or the insulin abnormality process.

5. The method of claim 1, wherein the user device is an internet of things (IOT) sensor, a smart watch, or a mobile device.

6. The method of claim 1, wherein the first service is the physician service, and
wherein triggering the emergency service based on the determination of whether to trigger the physician service comprises triggering the emergency service based on the determination to not trigger the physician service.

7. The method of claim 1, further comprising:
determining services within the aggregated updated contextual intelligent process; and
updating the one or more contextual artificial intelligence algorithms based on comparing the determined services from the aggregated updated contextual intelligent process with expected services.

8. The method of claim 7, wherein the one or more contextual artificial intelligence algorithms comprises one or more neural networks, and wherein updating the one or more contextual artificial intelligence algorithms is based on one or more loss functions.

9. The method of claim 1, wherein triggering the emergency service further comprises triggering an emergency contact service, wherein triggering the emergency contact service comprises notifying an emergency contact of the user of the user's medical condition.

10. The method of claim 9, wherein triggering the emergency service further comprises triggering the physician service.

11. A contextual intelligence system, comprising:
a processor; and
a non-transitory computer-readable medium having processor-executable instructions stored thereon, wherein the processor-executable instructions, when executed, facilitate:
obtaining, from a user device, health information comprising a heart rate of a user and an insulin level of the user;
determining a plurality of health triggering events based on comparing the heart rate of the user with one or more first thresholds and the insulin level of the user with one or more second thresholds;
obtaining event information associated with the user;
determining, based on the plurality of health triggering events, a plurality of contextual intelligent processes, wherein the plurality of contextual intelligent processes comprises a heart rate abnormality process associated with the heart rate of the user and an insulin abnormality process associated with the insulin level of the user, wherein each of the plurality of contextual intelligent processes comprises a sequence of actions, and wherein the sequence of actions comprises invoking a first service indicating a first application programming interface (API) hosted on a first computing platform and a determination of whether to trigger a physician service;
retrieving one or more contextual artificial intelligence algorithms;
inputting the plurality of health triggering events, the event information, and each of the plurality of contextual intelligent processes into the one or more contextual artificial intelligence algorithms to generate a plurality of updated contextual intelligent processes, wherein the plurality of updated contextual intelligent processes comprises an updated heart rate abnormality process and an updated insulin abnormality process;
aggregating the plurality of updated contextual intelligent processes into an aggregated updated contextual intelligent process comprising a single sequence of actions, wherein the aggregated updated contextual intelligent process comprises at least one new service indicating a second API hosted on a second computing platform that is different from the first computing platform, wherein the at least one new service comprises triggering an emergency service based on the determination of whether to trigger the physician service; and
performing the aggregated updated contextual intelligent process, wherein performing the aggregated updated contextual intelligent process comprises invoking the second API hosted on the second computing platform to trigger the emergency service, wherein triggering the emergency service comprises triggering an emergency health care provider service, and wherein triggering the emergency health care provider service comprises invoking the second API hosted on the second computing platform to notify an emergency provider to prepare the user for admission to the emergency provider.

12. The contextual intelligence system of claim 11, wherein the second API replaces the first API within the aggregated updated contextual intelligent process.

13. The contextual intelligence system of claim 11, wherein the at least one new service is sequentially placed after the first service within the aggregated updated contextual intelligent process.

14. The contextual intelligence system of claim 11, wherein the aggregated updated contextual intelligent process removes a third API from the sequence of actions of the heart rate abnormality process or the insulin abnormality process.

15. The contextual intelligence system of claim 11, wherein the user device is an internet of things (IOT) sensor, a smart watch, or a mobile device.

16. The contextual intelligence system of claim 11, wherein the processor-executable instructions, when executed, further facilitate:
   determining services within the aggregated updated contextual intelligent process; and
   updating the one or more contextual artificial intelligence algorithms based on comparing the determined services from the aggregated updated contextual intelligent process with expected services.

17. The contextual intelligence system of claim 16, wherein the one or more contextual artificial intelligence algorithms comprises one or more neural networks, and wherein updating the one or more contextual artificial intelligence algorithms is based on one or more loss functions.

18. A non-transitory computer-readable medium having processor-executable instructions stored thereon, wherein the processor-executable instructions, when executed, facilitate:
   obtaining, from a user device, health information comprising a heart rate of a user and an insulin level of the user;
   determining a plurality of health triggering events based on comparing the heart rate of the user with one or more first thresholds and the insulin level of the user with one or more second thresholds;
   obtaining event information associated with the user;
   determining, based on the plurality of health triggering events, a plurality of contextual intelligent processes, wherein the plurality of contextual intelligent processes comprises a heart rate abnormality process associated with the heart rate of the user and an insulin abnormality process associated with the insulin level of the user, wherein each of the plurality of contextual intelligent processes comprises a sequence of actions, and wherein the sequence of actions comprises invoking a first service indicating a first application programming interface (API) hosted on a first computing platform and a determination of whether to trigger a physician service;
   retrieving one or more contextual artificial intelligence algorithms;
   inputting the plurality of health triggering events, the event information, and each of the plurality of contextual intelligent processes into the one or more contextual artificial intelligence algorithms to generate a plurality of updated contextual intelligent processes, wherein the plurality of updated contextual intelligent processes comprises an updated heart rate abnormality process and an updated insulin abnormality process;
   aggregating the plurality of updated contextual intelligent processes into an aggregated updated contextual intelligent process comprising a single sequence of actions, wherein the aggregated updated contextual intelligent process comprises at least one new service indicating a second API hosted on a second computing platform that is different from the first computing platform, wherein the at least one new service comprises triggering an emergency service based on the determination of whether to trigger the physician service; and
   performing aggregated updated contextual intelligent process, wherein performing the aggregated updated contextual intelligent process comprises invoking the second API hosted on the second computing platform to trigger the emergency service, wherein triggering the emergency service comprises triggering an emergency health care provider service, and wherein triggering the emergency health care provider service comprises invoking the second API hosted on the second computing platform to notify an emergency provider to prepare the user for admission to the emergency provider.

19. The non-transitory computer-readable medium of claim 18, the second API replaces the first API within the aggregated updated contextual intelligent process.

\* \* \* \* \*